US011751797B2

(12) United States Patent
Bentz et al.

(10) Patent No.: US 11,751,797 B2
(45) Date of Patent: *Sep. 12, 2023

(54) SYSTEM FOR SPATIAL AND TEMPORAL MAPPING OF NEURONS IN BRAIN TISSUE

(71) Applicant: Purdue Research Foundation, West Lafayette, IN (US)

(72) Inventors: Brian Zahler Bentz, Albuquerque, NM (US); Kevin J. Webb, West Lafayette, IN (US); Dergan Lin, West Lafayette, IN (US); Justin Alexander Patel, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 382 days.

This patent is subject to a terminal disclaimer.

(21) Appl. No.: 16/554,307

(22) Filed: Aug. 28, 2019

(65) Prior Publication Data

US 2020/0069238 A1 Mar. 5, 2020

Related U.S. Application Data

(60) Provisional application No. 62/724,054, filed on Aug. 29, 2018, provisional application No. 62/723,907, filed on Aug. 28, 2018.

(51) Int. Cl.
*A61B 5/00* (2006.01)
*A61B 90/00* (2016.01)

(52) U.S. Cl.
CPC .......... *A61B 5/4064* (2013.01); *A61B 5/0062* (2013.01); *A61B 5/0071* (2013.01);
(Continued)

(58) Field of Classification Search
CPC .......... A61B 2090/371; A61B 2503/40; A61B 5/0062; A61B 5/0071; A61B 5/0077; A61B 5/4064; A61B 90/37
See application file for complete search history.

(56) References Cited

U.S. PATENT DOCUMENTS 9,655,523 B2 * 5/2017 Hillman ................ G01J 3/2889
2008/0079802 A1 * 4/2008 Nilson ................ G01N 21/763
348/44

(Continued)

OTHER PUBLICATIONS

Richard Robinson, "Short Stimulus, Long Response: Sodium and Calcium Dynamics Explain Persistent Neuronal Firing," Dec. 16, 2015, PLOS Biology (Year: 2015).*

(Continued)

*Primary Examiner* — Angela M Hoffa
*Assistant Examiner* — Maria Christina Talty
(74) *Attorney, Agent, or Firm* — Piroozi-IP, LLC

(57) ABSTRACT

A system for spatially mapping neurons in brain tissue is disclosed which includes a source of light configured to be shone on a subject at a first wavelength causing emission of light at a second wavelength from generating calcium when one or more neurons are firing, an optical filter configured to allow passage of light having the second wavelength, an image capture device configured to capture images of the brain tissue at the second wavelength, and a processor with software configured to establish a spatial model for localizing one or more neurons where captured images are used to iteratively adjust parameters of the model to thereby minimize error between generated and captured images.

9 Claims, 16 Drawing Sheets
(12 of 16 Drawing Sheet(s) Filed in Color)

(52) U.S. Cl.
CPC ............ *A61B 5/0077* (2013.01); *A61B 90/37* (2016.02); *A61B 2090/371* (2016.02)

(56) References Cited

U.S. PATENT DOCUMENTS

| | | | |
|---|---|---|---|
| 2017/0003491 A1* | 1/2017 | Waller | G02B 21/367 |
| 2018/0177401 A1* | 6/2018 | Yang | G01N 21/6458 |
| 2018/0270474 A1* | 9/2018 | Liu | H04N 5/33 |

OTHER PUBLICATIONS

Gibson et al., Recent advances in diffuse optical imaging, 2005, Phys. Med. Biol. 50, R1.

Arridge, Optical tomography in medical imaging, 1999, Inverse Prob. 15, R41-R93.

Ye et al., Optical diffusion tomography using iterative coordinate descent optimization in a Bayesian framework, 1999, J. Opt. Soc. Am. A 16, 2400-2412.

Milstein et al., Statistical approach for detection and localization of a fluorescing mouse tumor in Intralipid, 2005, Appl. Opt. 44, 2300-2310.

Gaind et al., Localization of an absorbing inhomogeneity in a scattering medium in a statistical framework, 2007, Opt. Lett. 32, 3026-3028.

Ye et al., Modified distorted Born iterative method with an approximate Fréchet derivative for optical diffusion tomography, 1999, J. Opt. Soc. Am. A 16, 1814-1826.

Schweiger et al., The Toast++ software suite for forwardand inverse modeling in optical tomography, 2014, J. Biomed. Opt. 19,040801-040801.

Eggebrecht et al., Mapping distributed brain function and networks with diffuse optical tomography, 2014, Nature Photonics 8, 448.

\* cited by examiner

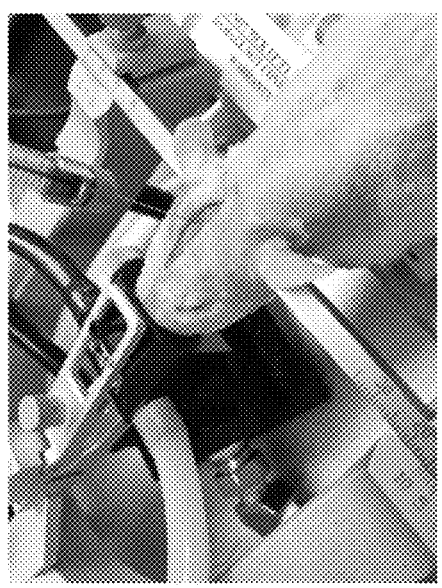
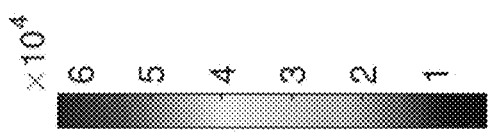
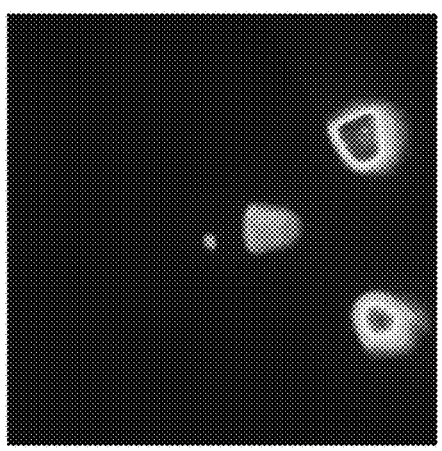
FIG. 2C
FIG. 2B
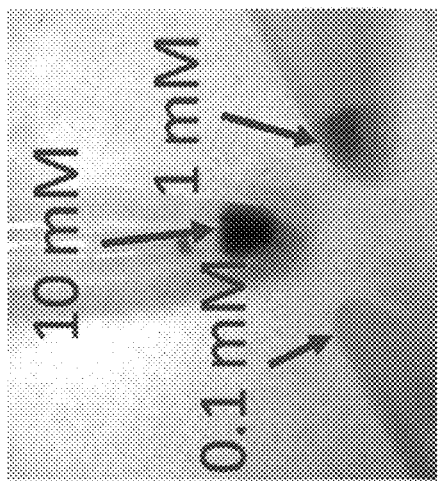
FIG. 2A

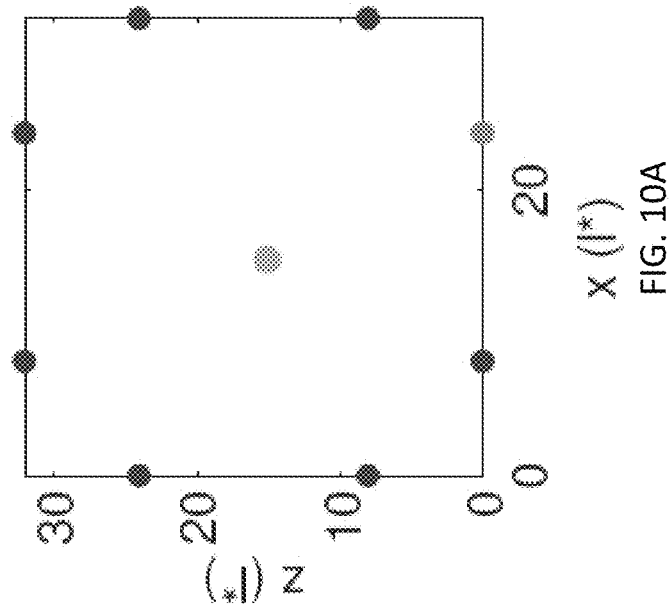
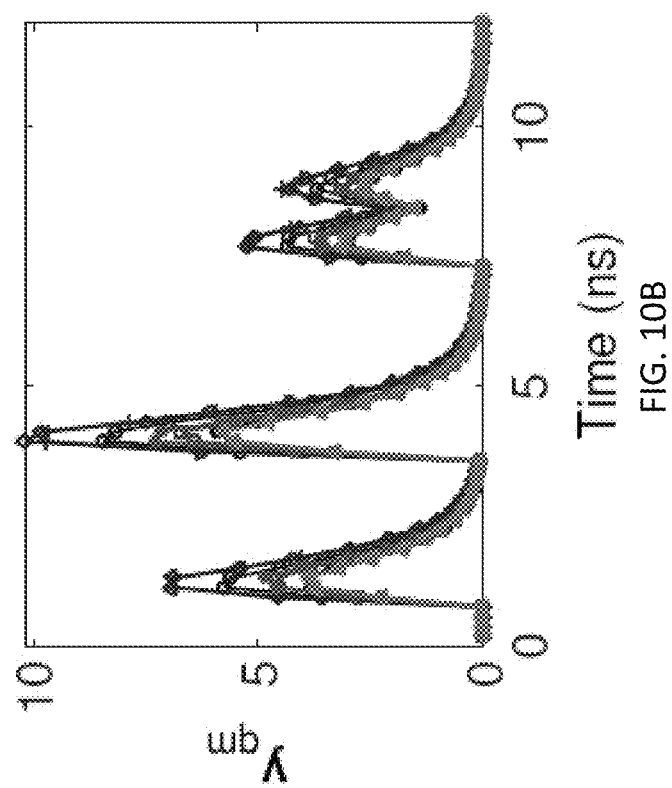
FIG. 10A
FIG. 10B

SYSTEM FOR SPATIAL AND TEMPORAL MAPPING OF NEURONS IN BRAIN TISSUE

CROSS-REFERENCE TO RELATED APPLICATIONS

The present patent application is related to and claims the priority benefit of U.S. Provisional Patent Application Ser. No. 62/723,907 filed Aug. 28, 2018, and U.S. Provisional Patent Application Ser. No. 62/724,054 filed Aug. 29, 2018, the contents of each of which are hereby incorporated by reference in its entirety into the present disclosure.

STATEMENT REGARDING GOVERNMENT FUNDING

This invention was made with government support under CA182235-01A1 awarded by the National Institutes of Health and CBET-0854249 and CISE-1218909 awarded by the National Science Foundation. The government has certain rights in the invention.

TECHNICAL FIELD

The present disclosure generally relates to brain mapping, and in particular to spatial and temporal mapping of neurons.

BACKGROUND

This section introduces aspects that may help facilitate a better understanding of the disclosure. Accordingly, these statements are to be read in this light and are not to be understood as admissions about what is or is not prior art.

There is substantial interest in fluorescence imaging which has become a standard tool in biomedical research. Methods such as confocal microscopy and multi-photon imaging have enabled high-resolution fluorescence imaging near the surface of tissues. Fluorescence imaging in deep tissue, where the propagation direction of light becomes randomized, presents a major challenge in optical imaging. Information is lost due to scatter and absorption, which hinders image formation. In deeper tissue, diffusive optical imaging methods suffer from low spatial resolution due to the strong attenuation of high-frequency information as light propagates through scattering media. This attenuation occurs whether the media is lossy (with absorption) or lossless (without absorption).

Of particular significance is the prospect of imaging calcium ($Ca^{2+}$) channel activity in neurons throughout the brain. Neuron activity involves $Ca^{2+}$ transport through channels in the cell body and then, after signal transfer along the axon, regulation of the neurotransmitter across the synaptic cleft in communication with the other neuron. Monitoring $Ca^{2+}$ signaling thus presents a direct picture of neuron activity. If it were possible to image $Ca^{2+}$ channel activity across the brain, the resulting maps would provide new understanding about how the brain works, and also answer fundamental questions about health and disease.

However, none of the available in vivo methods provide direct access to neurons, i.e., they measure secondary parameters. For example, Brain imaging with fMRI has been developed using the blood-oxygen-level dependent (BOLD) contrast, and this has become an important tool for brain science. However, blood oxygen levels provide low resolution and a slow and remote measure of brain signaling. Optical methods such as two-photon microscopy offer more direct access to a wider range of neurobiological information through optical contrast agents, but only provide information about the cortical surface of the brain visible through the use of cranial windows. However, for deep tissue, scattering of light remains a major hinderance.

Diffuse optical imaging methods have been developed to overcome the detrimental effects of scatter, enabling deep-tissue fluorescence imaging. In FDOT, computational imaging allows the formation of volumetric images of the absorption, scatter, and fluorescence from boundary measurements. Fundamentally, these methods detect what have become known as diffuse photon density waves (DPDW's) emanating from excitation or fluorescent sources. For typical measurements and tissues, the wavelength of a DPDW is a few centimeters, and measurements are made in the near field. Considering the angular spectrum of DPDW's, all the spatial frequencies propagate to the detector, however they are highly attenuated, even without absorption. This causes a severe reduction in spatial resolution with depth into the medium. The dependence of the spatial resolution on depth is nonlinear, but for typical tissues, measurement geometries, and beyond a depth of about 1 cm, spatial resolutions of about depth/2 have been achieved. We present a temporal localization method that circumvents earlier resolution limits. However, the object is modeled as a set of points, so other geometrical information is lost Therefore, there is an unmet need for a novel approach to image neurons at greater depths as a tool to better understand neurons and neuron activity.

SUMMARY

A system for spatially and temporally mapping neurons in brain tissue is disclosed. The system includes a source of light configured to be shone on a subject, the light source configured to illuminate brain tissue of a subject at a first wavelength, and in response cause emission of light at a second wavelength from generated calcium when one or more neurons are firing. The system also includes an optical filter configured to filter out light having the first wavelength and allow passage of light having the second wavelength. The system also includes an image capture device configured to capture images of the brain tissue at the second wavelength. The system also includes a processor having software encoded on a non-transitory computer readable medium that is configured to capture at least one 2-dimensional (2D) image of a subject having a plurality of pixels. The processor is further configured to establish information about approximate location of the one or more neurons, identify a region of interest about the approximate location of the one or more neurons, establish a 3D topography data of the subject at least about the region of interest, map each pixel of the region of interest of the at least one 2D image to the 3D topography data, and selectively generate a 3D geometric spatial and temporal model that provides spatial and temporal neuron activity information based on physical properties of light propagation through the brain tissue based on the 3D topography data including a plurality of parameters defining the spatial-temporal model, and the spatial-temporal model adapted to provide a model representation of the at least one 2D captured image. The processor is also configured to compare the spatial-temporal modeled at least one 2D captured image to the captured at least one 2D image and generate an error signal representing a difference therebetween, iteratively adjust the plurality of parameters of the spatial-temporal model to minimize the error signal, and output location and timing of the one or more neurons within the brain tissue within the region of interest.

Another system for spatially mapping neurons in brain tissue is disclosed. The system includes a source of light configured to be shone on a subject, the light source configured to illuminate brain tissue of a subject at a first wavelength, and in response cause emission of light at a second wavelength generated by calcium when one or more neurons are firing. The system also includes an optical filter configured to filter out light having the first wavelength and allow passage of light having the second wavelength. The system further includes an image capture device configured to capture images of the brain tissue at the second wavelength. The system also includes a processor having software encoded on a non-transitory computer readable medium configured to capture at least one 2-dimensional (2D) image of a subject having a plurality of pixels. The processor is also configured to establish information about approximate location of the one or more neurons, identify a region of interest about the approximate location of the one or more neurons, establish a 3D topography data of the subject at least about the region of interest, map each pixel of the region of interest of the at least one 2D image to the 3D topography data, and selectively generate a 3D geometric spatial model that provides spatial neuron information based on physical properties of light propagation through the brain tissue based on the 3D topography data including a plurality of parameters defining the spatial model, the spatial model adapted to provide a model representation of the at least one 2D captured image. The processor is further configured to compare the spatial modeled at least one 2D captured image to the captured at least one 2D image and generate an error signal representing a difference therebetween, iteratively adjust the plurality of parameters of the spatial model to minimize the error signal, and output location and geometric configuration of the one or more neurons within the brain tissue within the region of interest.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2A is a CCD image of 10-, 1-, and 0.1-mM solutions of ATTO647N in Dimethyl Sulfoxide (DMSO).

FIG. 2B is a CCD fluorescence image of ATTO647N from FIG. 2A.

FIG. 2C is a photograph of injecting 2 µL of the 1-mM solution if ATTO647N in Phosphate-Buffered Saline (PBS) into a rat.

FIGS. 10A and 10B are graphical representation of the problem geometry as in FIGS. 8A and 8B, where the positions of the excitation source (green), detectors (red), and fluorophores (cyan) are shown (FIG. 10A) as well as the simulated noisy data from the four inhomogeneities with various delays (FIG. 10B).

DETAILED DESCRIPTION

Figure 1:
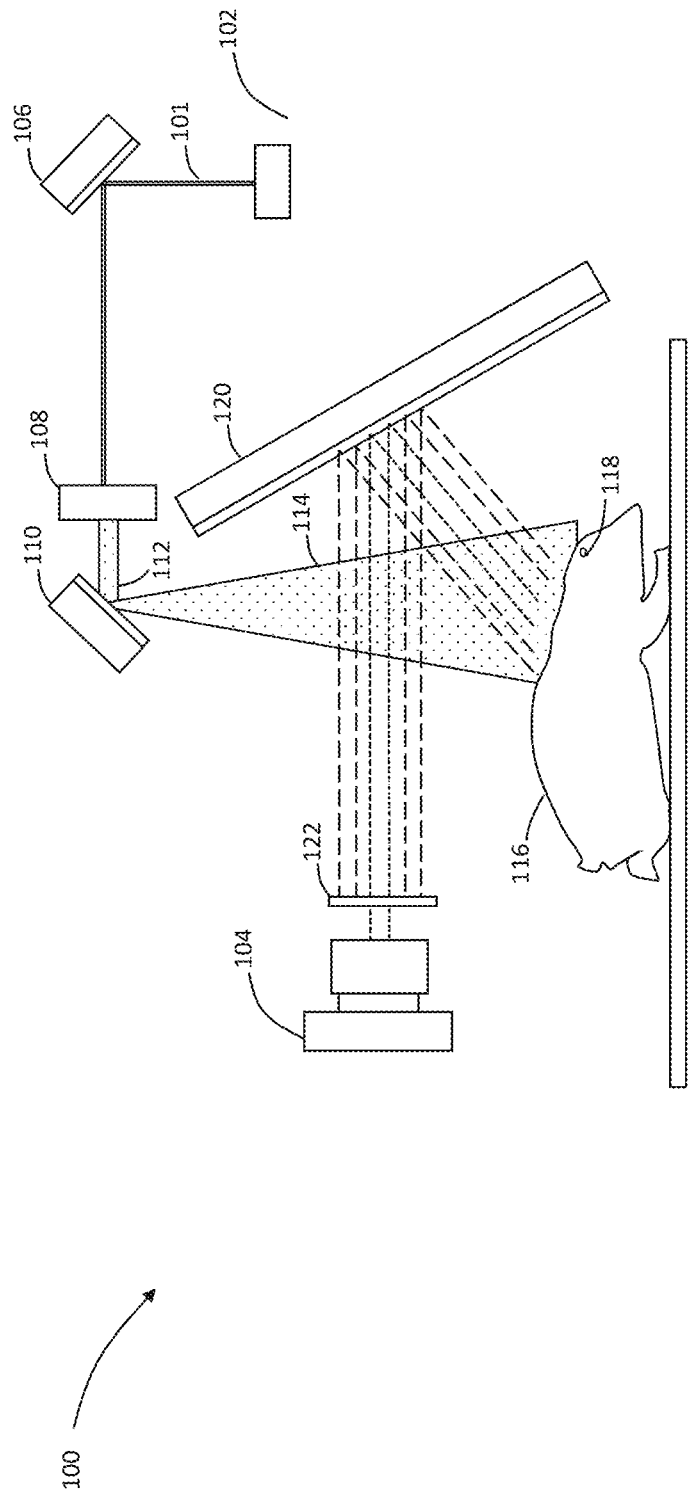
FIG. 1 is a schematic of a mapping system, according to the present disclosure, for mapping, including a light source, an image capture device, and an optical filter.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 90%, within 95%, or within 99% of a stated value or of a stated limit of a range.

A novel imaging approach is provided in the present disclosure that relies on treating fluorescent emitters whose signals vary in time as a set of point sources, and uses measurements of multiply scattered light as a function of time to find their locations to high precision. This novel approach presents the opportunity to directly image neurons throughout the brain of a small mammal, which should provide new understanding for neuroscience. This novel arrangement should also allow for imaging in other dynamic source situations in a cluttered environment.

Advantageously, $Ca^{2+}$ fluorescence and FRET sensors have been developed for in vitro studies. The principle is that calcium ($Ca^{2+}$) modulates the fluorescence emission or the energy transfer from the donor to the acceptor in the case of FRET, thereby encoding concentration information in the fluorescence that can be detected. The temporal modulation of the fluorescence therefore reports on calcium channel activity. However, with optical excitation using a laser, both the excitation light and the emitted fluorescence are multiply scattered. Computational imaging of fluorescence and FRET is possible with a forward model, such as the diffusion equation, using a suitable cost function, discussed below, but the spatial resolution achieved precludes being able to resolve individual neurons in deep tissue. By representing the local $Ca^{2+}$ fluorescent reporter as a point emitter or point absorber (the donor emission can reduce due to FRET), the present disclosure provides a framework suitable for localization using a forward model. Thus, high spatial resolution, where each reporter can be imaged to high resolution, under the assumption that there is distinct temporal modulation (due to the neuronal activity) is provided. This approach uses an optimization framework with a forward model for the scattering medium.

The novel approach of the present disclosure includes a model describing the measured fluorescence intensity due to multiple sources of fluorescence within a highly scattering media. The model can then be used to localize fluorescence separated in space and distributed in time.

Prior to applying the model based on both spatial and temporal solutions, it is important to show fluorescent signals can be detected from deep within the brain. To this end, ATTO647N was chosen as a dye because of its attractive optical properties. Its peak excitation and emission wavelengths are 646 nm and 664 nm, respectively. According to an optical set shown in FIG. 1, an image system 100 is shown. The imaging system 100 includes a light source 102 and a detector 104. The detector 104 is an image capture device, e.g., a charge-coupled device (CCD) or a plurality of photodiodes. The light source can be a laser configured to emit light 101 at a wavelength of interest. Light 101 is redirected by a mirror 106 which is then incident on spreader 108. The spreader 108 or beam expander spreads the collimated light 101 into a broad-area illumination 112 that is incident on a mirror 110 and reflected in a cone of light 114 onto to a subject, in this case a mouse 116. The mouse 116 has a window (not shown) opened in the skull to gain optical access to the brain tissue. A small amount of dye 118 deep within tissue is made present (e.g., by injecting the dye into the brain). Light 114 is scattered and diffused into the tissue of the mouse 116. The dye 118 includes a fluorophore such that diffused light reaching the dye 118 excites the fluorophore such that light of a different known wavelength is emitted. The emitted fluoresced light along with light scattered from the mouse 116 are incident on a mirror 120 and reflected onto a filter 122 that filters out non-fluorescent wavelength light and only allows the fluoresced light through and onto the detector 104.

Figure 3D:
FIGS. 3C and 3D are a CCD image under room light conditions after injection, where the surgical sutures are visible, and a CCD fluorescence image through the bandpass filter after injection, respectively.
Figure 3D:
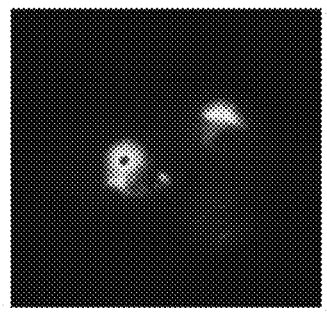
Figure 3C:
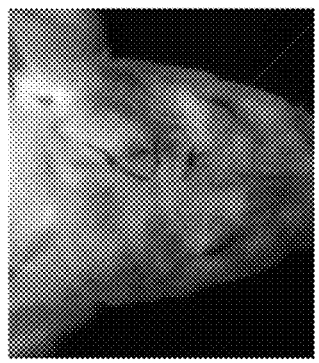
Figure 3B:
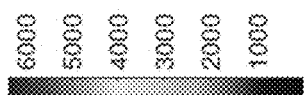
FIGS. 3A and 3B are a CCD image under room light condition prior to injection and a CCD fluorescence image through the filter of FIG. 1 before injection.
Figure 3B:
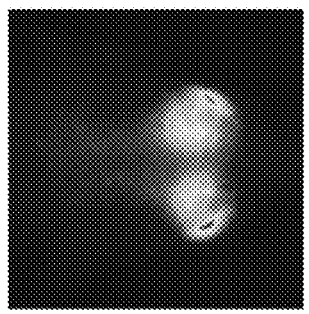
Figure 3A:
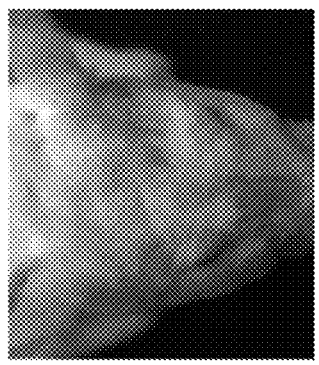

The detector 104 is coupled to a processor (not shown) which has analyzing software on a non-transitory computer readable medium configured to determine the characteristics of the dye 118 (or other tissue that has been treated with a florescent material). An OD6 emission bandpass filter centered at 676 nm with a 29-nm bandwidth (EDMUND OPTICS®-86-996) was used as the filter 122 to measure the fluorescence emission. The dye 118 was excited by the expanded light from the EXR-20 filtered to 633 nm with a 10-nm bandwidth. The dye 118 is bright for its wavelength, with a quantum yield of 0.65 and a fluorescence lifetime of 3.5 ns. A 10-mM stock solution of 1 mg maleimide ATTO647N (868 g/mol) and 115-4 of PBS was prepared. The stock solution was used to form 50 µL aliquots at concentrations of 10-mM, 1-mM, and 0.1-mM, as shown in FIG. 2A, which is a CCD image of 10-, 1-, and 0.1-mM solutions of ATTO647N in Dimethyl Sulfoxide (DMSO) that were prepared from a stock solution. Significant quenching was observed at high concentration, as seen in FIG. 2B, which is a CCD fluorescence image of ATTO647N from FIG. 2A. For this reason, 2-4 of the 1-mM solution was used for stereotaxic injections, as shown in FIG. 2C, which is a photograph of injecting 2 µL of the 1-mM solution if ATTO647N in Phosphate-Buffered Saline (PBS) into the rat. The injection site was 5 mm across and 2 mm back from the Bregma, and the depth was 8 mm below the skull surface. In order to study the signal level, CCD fluorescence images of a rat were captured before and after injection of ATTO647N. First, the top of the rat was imaged, as shown in FIGS. 3A and 3B, which are a CCD image under room light condition prior to injection, and a CCD fluorescence image through the bandpass filter 122 before injection. Next, the 1-4 solution of ATTO647N was stereotaxically injected into the substantia nigra (about 8 mm below the surface of the skull) at a rate of 0.2 µL/minute. After injection the needle was kept in place for 10 minutes before being slowly removed. The tissue was sutured and washed, and the top of the rat was imaged again, as shown in FIGS. 3C and 3D which show a CCD image under room light conditions after injection, where the surgical sutures are visible, and which shows a CCD fluorescence image through the bandpass filter after injection, respectively. A strong fluorescence signal is visible above the injection site. The same signal was observed after cinching the skin and shifting it, ensuring that the signal emanated from deep within the brain and not from near the tissue surface. This result demonstrates that it is possible to detect fluorescence within the brain for in vivo studies of, for example, the substantia nigra.

Figure 4:
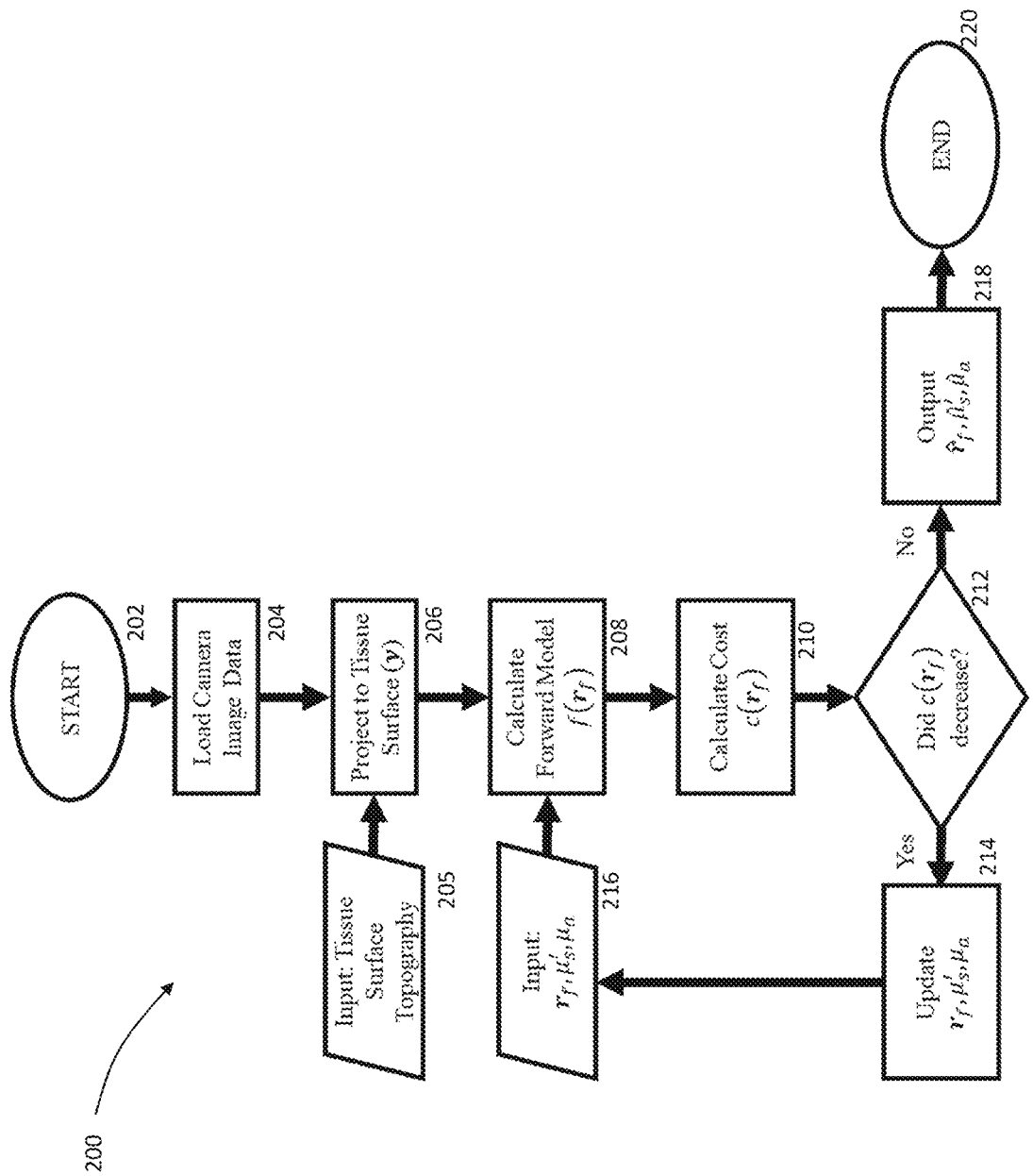
FIG. 4 is a flowchart describing steps of modeling, according to one embodiment of the present disclosure.

The injected ATTO647N was localized with a process 200 described in FIG. 4. Prior to describing the steps in the process 200 shown in FIG. 4, a discussion of a diffusion model for describing light transport in highly scattering media is provided using spatial-only light scattering. Thereafter, the model is further developed for temporal discrimination of neuron activity.

In the presence of fluorescence, two coupled diffusion equations can be used to model the propagation of photons at the fluorophore excitation wavelength, $\lambda_x$ (i.e., the wavelength of light that causes excitation of the fluorophore), and the fluorophore emission wavelength, $\lambda_m$ (i.e., the wavelength at which the fluorophore emits light once excited). For exp(jωt) time variation, the coupled diffusion equations are:

$$\nabla \cdot [D_x(r)\nabla \phi_x(r, \omega)] - \left[\mu_a(r) + \frac{j\omega}{c}\right]\phi_x(r, \omega) = -S_x(r; \omega), \quad (1)$$

$$\nabla \cdot [D_m(r)\nabla \phi_m(r, \omega)] - \left[\mu_a(r) + \frac{j\omega}{c}\right]\phi_m(r, \omega) = -\phi_x(r, \omega)S_f(r; \omega), \quad (2)$$

where r denotes the position,
ϕ(r, ω) (W/mm$^2$) is the photon flux density,
ω is the angular modulation frequency,
D=1/[3(µ'$_s$+µ$_a$)] (mm) is the diffusion coefficient,
µ'$_s$ (mm) is the reduced scattering coefficient,
µ$_a$ (mm) is the absorption coefficient,
c is the speed of light in the medium,
the subscripts x and m denote parameters at the fluorophore excitation and emission wavelengths, $\lambda_x$ and $\lambda_m$, respectively,
$S_x$ (W/mm$^3$) is the excitation source term, and
$S_f$=η(1+jωτ)$^{-1}$ (mm$^{-1}$) is the fluorescence source term.

Equations (1) and (2) are coupled through the $\Phi_x(r,\omega)$ term on the right hand side of (2). These equations represent a set of partial differential equations (PDE), that can be solved numerically using the Green's function, as known to a person having ordinary skill in the art. In an infinite homogeneous space, the diffusion equation's Green's function is $$g(r, r') = \frac{e^{-jk|r-r'|}}{4\pi|r-r'|} \tag{3}$$

where r' is the position of a point source, and $k^2 = -\mu_a D - j\omega/(Dc)$, where $\mu_a$ and D can be calculated at $\lambda_x$ or $\lambda_m$ in (1) or (2), respectively. Equation (3) represents the numerical solution of propagation of photons.

Based on equations (1), (2), and (3), a model can thus be generated based on the assumption that tissue surrounding the dye is homogeneous and thus diffuses light uniformly. To this end, Equations (1) and (2) can be solved on an unstructured finite element method (FEM) mesh. However, the FEM solution requires extensive computational time, limiting its application in an operating environment. For this reason, a closed-form analytic solution can be adopted that allows fast computation.

Figure 5:
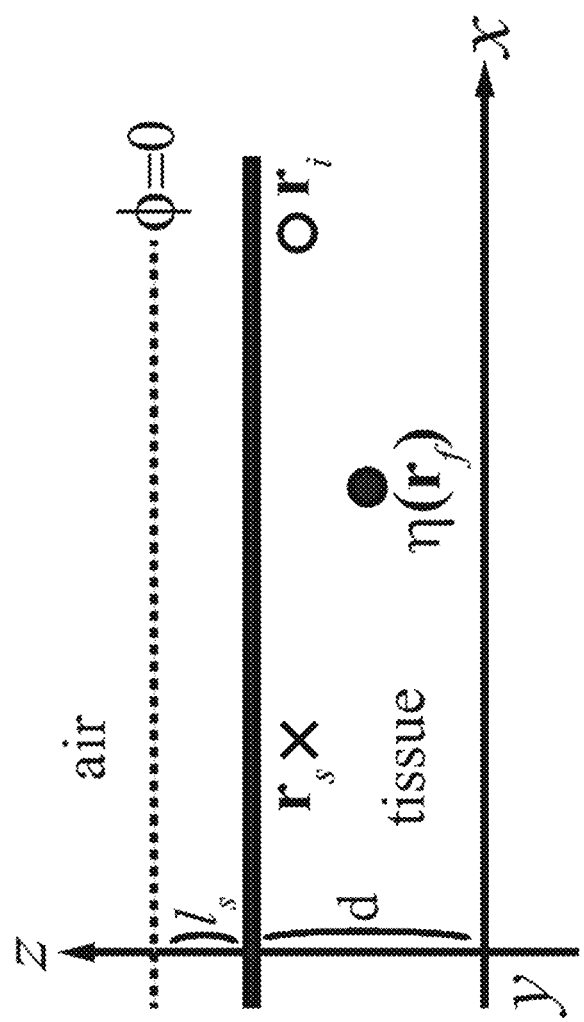
FIG. 5 is a schematic of a geometry relevant to the imaging system of the present disclosure.

Referring to FIG. 5, a schematic of a geometry relevant to the imaging system of the present disclosure is shown. FIG. 5 represent model geometry for a single tissue boundary, where r=(x,y,z) with the y-axis is going into the page. The thickness of the tissue, denoted as d, is assumed to be large such that the diffusion model holds. An excitation source (X) at $r_s$ and a fluorescence emission detector (O) at $r_i$ are placed one scattering length $l_s=3D$ away from the tissue boundary. The dye, i.e., source of florescence is at an unknown position $r_f$. To simulate semi-infinite planar geometry, a zero-flux ($\varphi=0$) boundary condition is used with $l_s=0.503D$. In addition it is assumed that a laser excitation point source is located at $r_s$, giving $S_x(r, \omega)=S_o\delta(r-r_s)$, where $S_o$ is the laser excitation power density (W/mm$^2$) and $\delta$ is the Dirac delta function. It is also assumed that N point detectors at $\lambda_m$ are located at positions $r_i$, where i is an index form 1 to N. It is also assumed that a single fluorescence point source is located at $r_f$ such that $S_f(r, \omega)=\eta_f\mu_{af}\delta(r-r_s)$, where $\eta_f$ and $\mu_{af}$ are the quantum yield and absorption of the fluorophore, respectively. Localization of the dye means to estimate $r_f$. The $i^{th}$ forward model solution $\tilde{f}_i$, of the fluorescence emission measured at $r_i$ is then:

$$\tilde{f}_i(r_r) = w[g_m(r_f r_i) g_x(r_s, r_f)], \tag{4}$$

$$= w f_i(r_f), \tag{5}$$

where w is a multiplicative constant that incorporates $\eta_f$, $\mu_{af}$, $S_o$, and the efficiency of light coupling into the medium, $g_x(r_s, r_f)$ represent the diffusion equation Green's function for (1) at $\lambda_x$, and $g_m(r_f r_i)$ represent the diffusion equation Green's function for (2) at $\lambda_m$. The Green's functions are derived by assuming a single boundary exists such that $r_s$ and $r_i$ are on the boundary and $r_f$ is below the boundary, as shown in FIG. 5. An extrapolated zero-flux boundary condition is enforced using image sources. Analytic expressions for $g_x(r_s, r_f)$ and $g_m(r_f r_i)$ are found using (3) and summing the contributions of the sources. It should be noted that $f_i(r_f)$ depends nonlinearly on $r_f$.

If a fluorescence source is present, its position can be estimated by finding the value of $r_f$ that minimizes the cost function $$c(r_f) = \min_{w} \|y - wf(r_f)\|_{Y^{-1}}^2, \tag{6}$$

where y is a vector of N measurements, $f(r_f)$ is a vector of N forward calculations $f_i(r_f)$ from (5), $\gamma=\alpha\text{diag}[|y_1|, \ldots, |y_N|]$ is the noise covariance matrix, for which we assume a shot noise model characterized by $\alpha$. For an arbitrary vector v, $\|v\|_{Y^{-1}}^2 = v^H \gamma^{-1} v$.

where H denotes the Hermitian transpose. Only the case where a single excitation source is present at position $r_s$ is considered. In this case, $g_x(r_s, r_f)$ at $r_f$ is constant, and can therefore be pulled out of $f(r_f)$, giving $$c(r_f) = \min_{w} \|y - w g_x(r_s, r_f) h(r_f)\|_{Y^{-1}}^2, \tag{7}$$

where $h_i(r_f)=g_m(r_f, r_i)$ is the $i^{th}$ component of $h(r_f)$. Because $g_x(r_s, r_f)$ is a constant at $r_f$, it can be incorporated into w as $$c(r_f) = \min_{w_s} \|y - w_s h(r_f)\|_{Y^{-1}}^2, \tag{8}$$

For localization, one goal is to find the $r_f$ that minimizes (8), and we note that the inverse problem is linear in $w_s$ and nonlinear in $r_f$. Equation (8) can therefore be minimized using a two-step procedure. First, we set the derivative of $\|y - w_s h(r_f)\|_{Y^{-1}}^2$ with respect to $w_s$ equal to zero and solve for $w_s$, resulting in $$\widetilde{w_s}(r_f) = \frac{h^T(r_f) Y^{-1} y}{h^T(r_f) Y^{-1} h(r_f)}, \tag{9}$$

$$c(r_f) = \min_{w_s} \|y - \widetilde{w_s}(r_f) h(r_f)\|_{Y^{-1}}^2, \tag{10}$$

Second, we calculate (10) at a set of positions $r_f$ within a region of interest that encompasses the true location. The maximum likelihood estimates are then $$\widetilde{r_f} = \arg\min_{r_f} c(r_f), \tag{11}$$

$$\widehat{w_s} = \widetilde{w_s} = (\widetilde{r_f}), \tag{12}$$

An important step in our derivation that differentiates it from previous derivations is the incorporation of $g_x(r_s, r_f)$ into $w_s$. This step implies that the inverse problem can be solved without consideration or modeling of the excitation source, and only $g_m(r_f, r_i)$ needs to be computed for the forward model. This is of great utility because complicated illumination patterns (such as an expanded beam) do not need to be modeled.

Figure 6C:
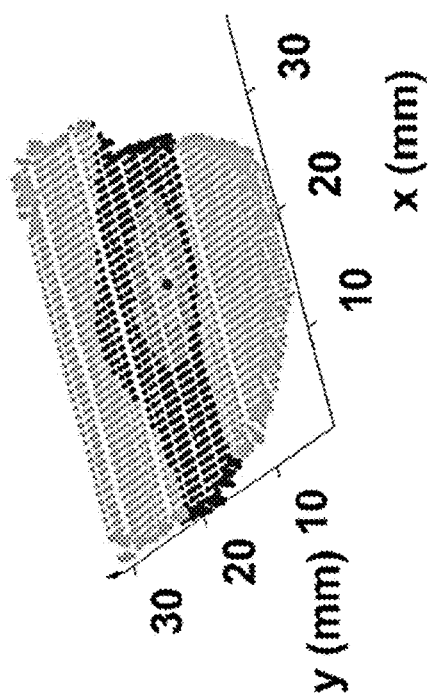
FIGS. 6B and 6C are plots of nodes from the Cartesian grid within thin slices at y=17 mm and z=24 mm, respectively, where the estimated node position of the ATTO647N is plotted as the red point.
Figure 6B:
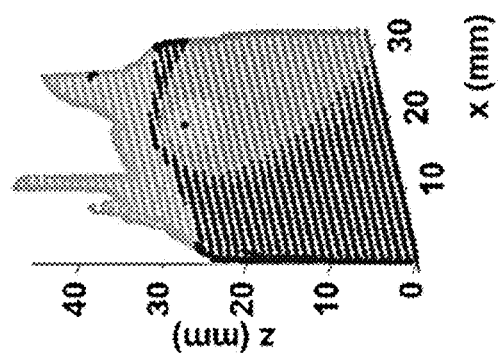
Figure 6A:
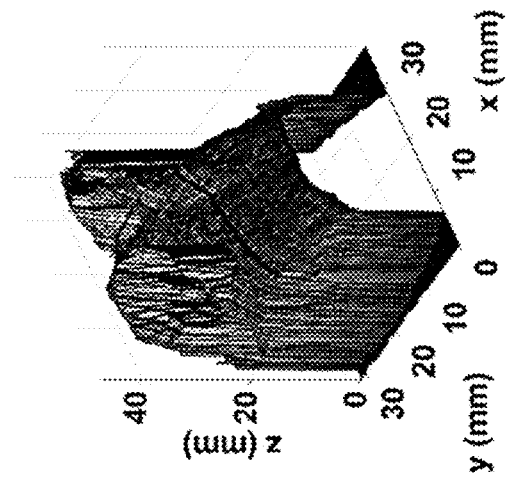
FIG. 6A is a 3D topography of a rat's head.
Figure 6E:
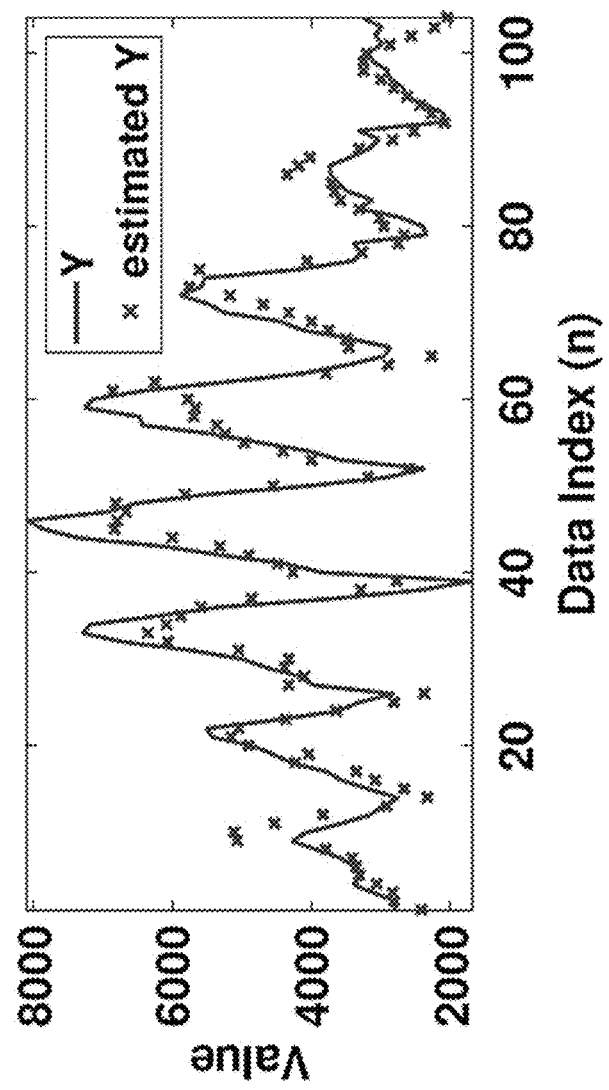
FIG. 6E, is a plot (value vs. data index) of the measured data vector y against the estimated y.
Figure 6D:
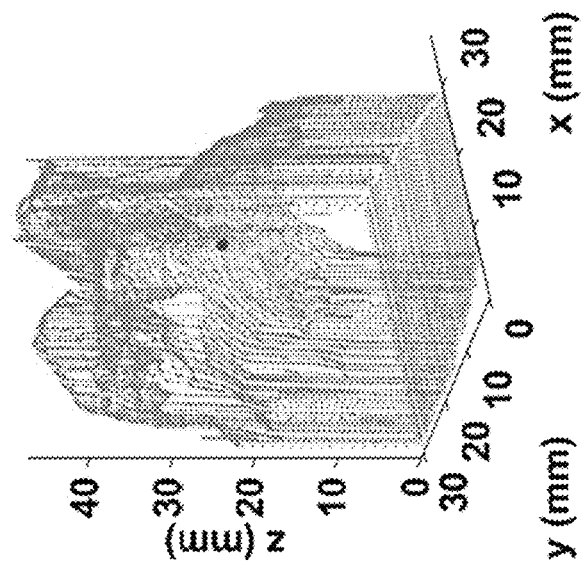
FIG. 6D is a plot of a node boundary obtained using the 3D topography laser line scan and the estimated location in a Cartesian coordinate system (X-Y-Z).

A 3D topography of the rat's head is shown in FIG. 6A, which was used to define a region of interest and place 104 detectors in the region above the injection site. The scatter was fixed at $\mu'_s=2.0$ mm$^{-1}$, and $\mu_a$ was ranged from 0.02 mm$^{-1}$ to 0.05 mm$^{-1}$ in increments of 0.005 mm$^{-1}$. A 3D profile is thus generated using the laser line scan of the rat. Along the y-axis, the rat eye are at about y=0 mm, and the ears are between about y=20 mm and y=30 mm. The 3D profile was discretized into 124,047 nodes, and the cost was calculated at each node position The results of the localization are presented in FIG. 6B-6E. The position that minimized the cost was (19.8, 16.6, 24.0) mm, giving an estimated depth of about 8.3 mm below the tissue surface. FIGS. 6B and 6C show plots of nodes from the Cartesian grid within thin slices at y=17 mm and z=24 mm, respectively, where the estimated node position of the ATTO647N is plotted as the red point. Each node is plotted as a different color that depends on the cost calculated at that position, with $\mu_a$ fixed at the value that minimized the overall cost. The estimated depth of the ATTO647N is about 8.3 mm below the tissue surface. Each other node is plotted as a different color that depends on the cost calculated at that position. Yellow, green, blue, and cyan nodes have costs above the minimum cost, 0.1 of the maximum cost, 0.25 of the maximum cost, and 0.4 of the maximum cost, respectively. FIG. 6D shows a plot of the node boundary obtained using the 3D topography laser line scan and the estimated location. In FIG. 6E, the measured data vector y is plotted with the estimated $\hat{y} = \widehat{w_s} h(\widehat{r_f})$. The surface is not as slowly varying as that of FIG. 4, and there is significant autofluorescence, causing errors in the fit. However, it was still possible to estimate the correct depth of the ATTO647N.

Referring to FIG. 4, the process 200 starts out at the start block 202 and proceeds to loading camera image data, block 204. This data represents the filtered (i.e., fluoresced light emitted from a source of fluorescence in an otherwise homogeneous tissue allowed to pass through the filter 122 (see FIG. 1)). This step represents capture of at least one 2-dimensional (2D) image of a subject having a plurality of pixels. A region of interest is thus identified about the dye in an otherwise homogeneous tissue. Next a 3D topography data of the subject is established as shown in block 205. This topography data is established by one of many approaches known to a person having ordinary skill in the art. For example, laser scanning of the subject can be used to establish the 3D topography data. Another example is a stereoscopic approach using stereo cameras. The 3D topography data is fed to the processor which maps the 2D image at least about the region of interest to the 3D topography data. This is done in block 206. Next in block 208 a forward model solution is generated. The model is a mathematical model representing physical properties of light propagation through the source of fluorescence and homogeneous tissue based on the 3D topography data including a plurality of parameters defining the model. The model is adapted to provide a model representation of the at least one 2D captured image. Next in block 210 a cost function is calculated based on comparison of the modeled at least one 2D captured image to the actual captured of the at least 2D image. The cost function represents an error signal representing a difference therebetween. In the decision block 212 the cost function is compared to the last iteration; if the cost decreased (i.e., still not at the minimum), then the parameters of the model ($r_f$, $\mu_s'$, and $\mu_a$) are updated in block 214 and provided to the model as updates in block 216. Otherwise (i.e., the cost function is at the minimum), the parameters are provided to the model at block 218, and the optimization of the model ends in block 220. The model can then output the location and geometric dimensions of the dye to be used for further processing (e.g., studying neurons and how they fire).

The approach outlined in FIG. 4 and the localization of dye within a mammalian brain tissue can be used to for imaging calcium sensitive dyes to monitor activity of neurons in the brain. Signaling between neurons is accompanied by an increase in the local concentration of calcium, which can modulate fluorescence emission. In principle, measurements with a CCD camera for shallow detection or a fiber array inserted into brain tissue for deep-tissue monitoring with short integration times could provide data from individual neurons such that each could be localized, providing an image of the entire animal brain or brain surface in vivo. These images of the entire brain could be used to form correlation maps, which are useful for studying neurological diseases and developing treatments. This type of imaging could provide new information on chemical and electrical neural activity because available in vivo methods, such as fMRI, provide only indirect access to neurons by measuring secondary parameters.

With the spatial localization fully described, we now turn our attention to a combination of spatial localization and temporal discrimination between various neurons. Similar to equations (1) and (2), we begin the derivation with equations (13) and (14) which represent a coupled diffusion model in the time domain.

$$\frac{1}{v}\frac{\partial}{\partial t}\phi_x(r, t) - \nabla \cdot [D_x(r)\nabla \phi_x(r, t)] + \mu_{a_x}(r)\phi_x(r, t) = S_x(r; t) \quad (13)$$

$$\frac{1}{v}\frac{\partial}{\partial t}\phi_m(r, t) - \nabla \cdot [D_m(r)\nabla \phi_m(r, t)] + \mu_{a_m}(r)\phi_m(r, t) = \phi_x(r, t) * S_f(r; t). \quad (14)$$

where r denotes the position,
$\varphi$(W/mm$^2$) is the photon flux density,
$\mu_a$ (mm$^{-1}$) is the absorption coefficient,
D=1/[3($\mu_a+\mu_s'$)](mm) is the diffusion coefficient,
$\mu_s'=\mu_s(1-g)$ (mm$^{-1}$) is the reduced scattering coefficient,
$\mu_s$ is the scattering coefficient (mm$^{-1}$),
g is the anisotropy parameter,
v=c/n is the speed of light in the medium, where
c is the speed of light in free space and
n is the refractive index,
the subscripts x and m, respectively, denote parameters at the excitation and emission wavelengths, $\lambda_x$ and $\lambda_m$, $S_x$(W/mm$^3$) is the excitation source term, $S_f$(1/s/mm) is the fluorescence source term, and
\* signifies a temporal convolution. Equations (13) and (14) can be transformed into an analytical solution represented by equation (15):

$$\phi_m(r_s,r_d,t) = \int g_{ra}(r',r_d,t)*D_f(r';t)*g_{ac}(r_s,r',t)dx' \quad (15)$$

Using the Green's function from equation (15), we can derive the cost function as provided in equation (16):

$$\phi_m(r_s, r_f, r_d, t) = \frac{v}{(4\pi D_m vt)^{3/2}} \exp\left(\frac{-|r_d - r_f|^2}{4D_m vt} - \mu_{a_m} vt\right) * \frac{\eta}{\tau_f}\exp\left(\frac{-t}{\tau_f}\right) * \frac{v}{(4\pi D_x vt)^{3/2}}\exp\left(\frac{-|r_f - r_s|^2}{4D_x vt} - \mu_{a_x} vt\right) \quad (16)$$

We can now write the fluorescence data vector expected from the diffusion model as f(R,τ), which is $$f(r,\tau)=[f_{111}, \ldots f_{11N}, f_{121}, \ldots f_{12N}, \ldots f_{1M1}, \ldots f_{1MN}, f_{211}, \ldots f_{QMN}]^T. \quad (17)$$

And which is simplified as (18):

$$f(R,\tau) = F(R,\tau)\eta \quad (18)$$

The cost function based on both spatial and temporal error minimization thus is provided in (19):

$$c(R, \tau) = \min_{\eta} \|y - F(R, \tau)\eta\|_{\Upsilon^{-1}}^2, \quad (19)$$

where F represents both spatial and temporal functions, R represents the spatial parameter, and τ represents the temporal parameter. A complete derivation of the cost function is presented in Appendix A of the present disclosure, filed herewith.

Figure 7B:
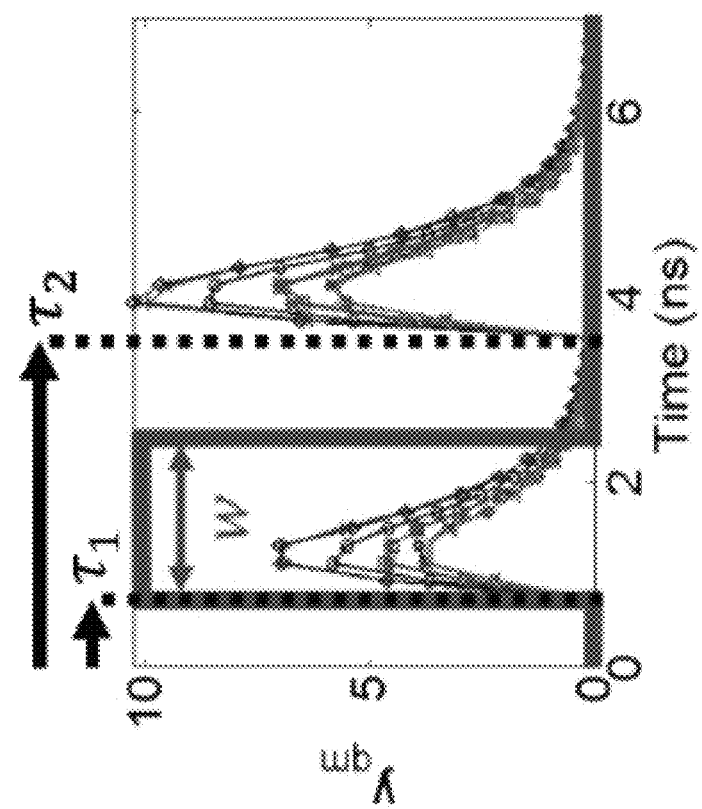
FIGS. 7A and 7B are temporal separation of fluorescent impulse responses of two emitters in two different cases.
Figure 7A:
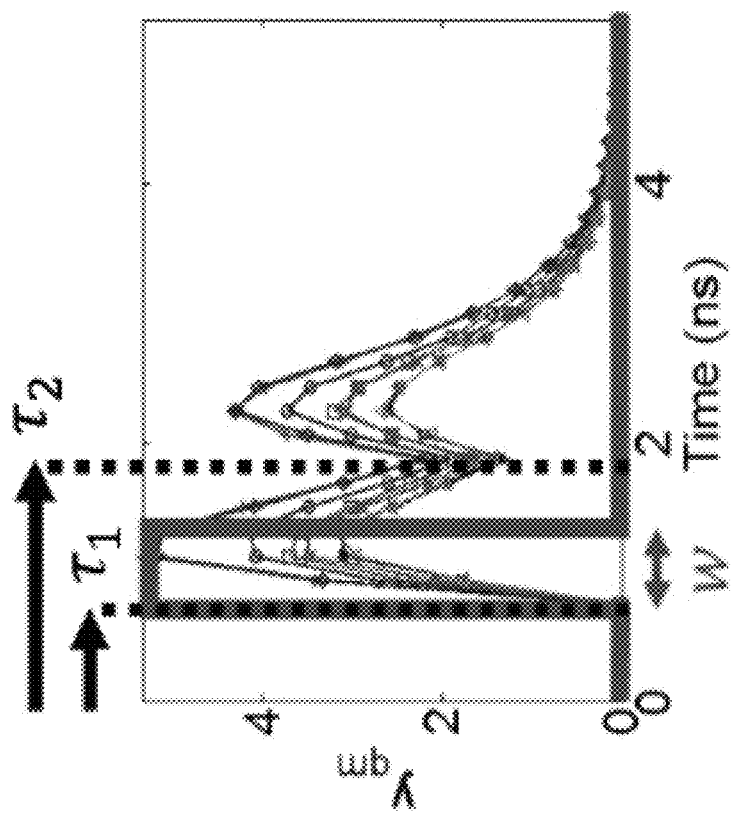

To minimize (19), a method that takes advantage of the causality is used. The approach allows us to avoid calculation of the basis functions at each $\tau_k$ and their inner products, alleviating the computational burden. We assume that each $\tau_k$ is unique, allowing temporal separation of the fluorescent impulse responses, as shown in FIGS. 7A and 7B for the case of two emitters. FIGS. 7A and 7B show typical fluorescence temporal responses for one source and seven detectors (Q=1, M=7). The 7 different symbols and corresponding colors represent different source detector measurement pairs. The time axis is a discrete set of points $t_1 \ldots, t_N$, with T seconds between sample points. FIG. 7A shows a case where the delay $\tau_2$ is short, causing substantial overlap due to superposition. FIG. 7B shows a case where the delay $\tau_2$ is long such that the detected fluorescence decays substantially before the next fluorescence response. We show that localization of the source of fluorescence is possible in both cases. In FIG. 7A the temporal responses from two point fluorophore locations in a scattering domain are measured to be displaced in time but overlapping, whereas in FIG. 7B they are distinct. We consider the general case where the delays Tk are not large enough for the fluorescence to decay to noise before the start of the next response, as shown in FIG. 7A. The discretized measurement data leads to a temporal sampling period T and we consider a temporal window w, illustrated in FIGS. 7A and 7B, including an integer number of samples separated in time by T.

Considering that $\eta_k$ could be estimated using data within a temporal window starting at $t_o = \tau_k$ with $w < \tau_{k+1} - \tau_k$, one can assume that the data within the temporal window w comes from a single fluorophore at $r_{f_k}$. A simplified cost function based on (19) can then be written as $$c_k(r_{f_k}, \tau_k) = \min_{\eta_k} \|y_k - \eta_k f_k(r_{f_k})\|_{\Upsilon_k^{-1}}^2 \quad (20)$$

Equation (20) can be minimized using known techniques, including a two-step process described by (21):

$$\tilde{\eta}_k(r_{f_k}) = \frac{f_k^T(r_{f_k})\Upsilon_k^{-1} y_k}{f_k^T(r_{f_k})\Upsilon_k^{-1} f_k(r_{f_k})} \quad (21)$$

$$c_k(r_{f_k}, \tau_k) = \|y_k - \tilde{\eta}_k(r_{f_k})f_k(r_{f_k})\|_{\Upsilon_k^{-1}}^2$$

by setting the derivative of $\|y_k - \eta_k \cdot f_k(r_k)\|_{\Upsilon_k^{-1}}^2$ with respect to $\rho_k$ equal to zero. Equations (21) are then solved at positions $r_{f_k}$ of interest (within the time window w), and the kth fluorescent emitter's position and yield are estimated by $$\hat{r}_{f_k} = \arg\min_{r_{f_k}} c_k(r_{f_k}, \tau_k)$$

$$\hat{\eta}_k = \tilde{\eta}_k(\hat{r}_{f_k}).$$

In an experiment, where calibration scale factors are unknown, $\tilde{\rho}_k$ can be considered a nuisance parameter [38] where its estimate is no longer quantitative. Interestingly, if $\gamma^{-1}$ was an identity matrix, (21) would be equivalent to calculating the basis function weight in matching pursuit. Because of this, the localization method presented here could be considered a constrained version of matching pursuit that incorporates a noise model.

Figure 8B:
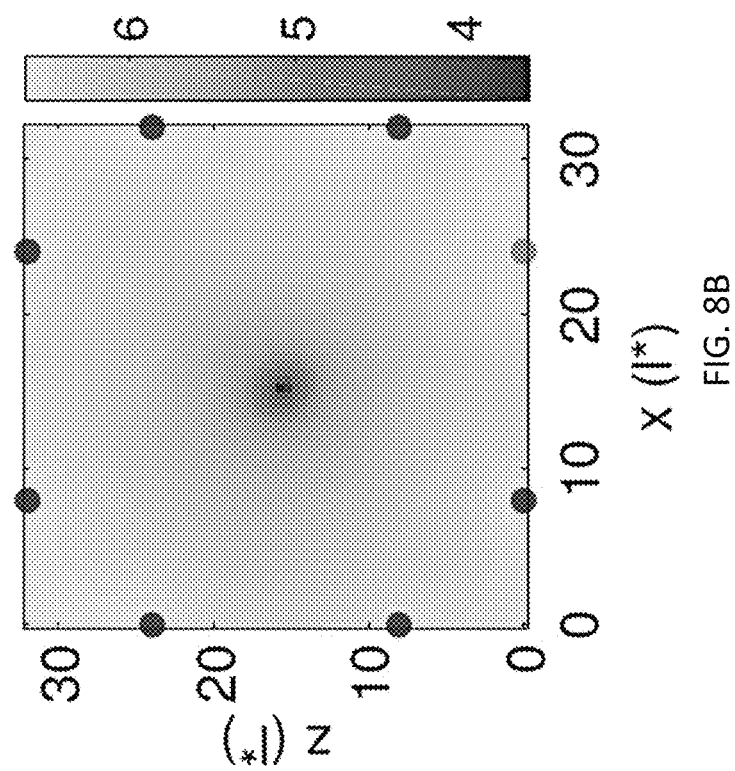
FIGS. 8A and 8B are localization of a single source of fluorescence using an (x,z) coordinate system.
Figure 8A:
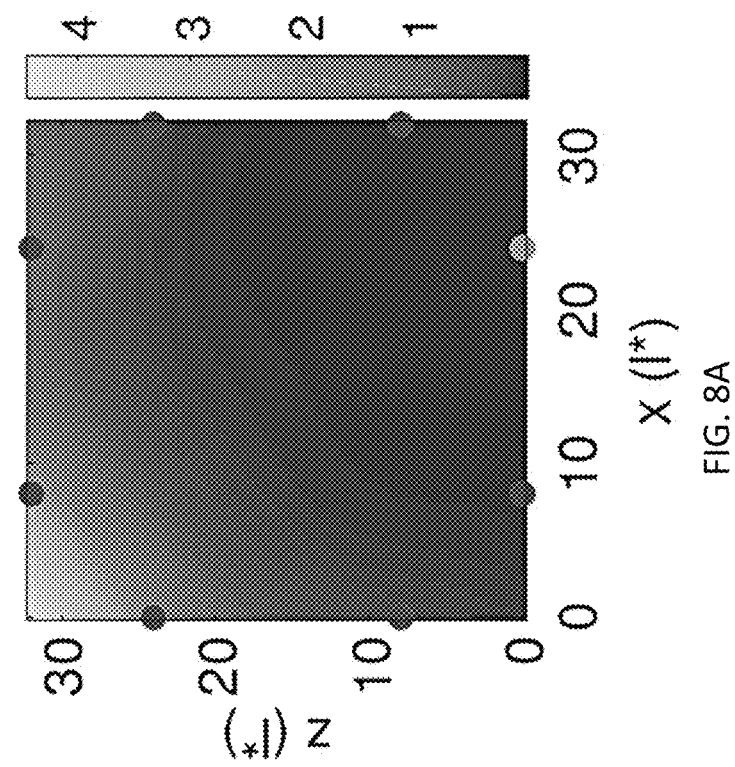

We demonstrate localization of a single source of fluorescence using optical properties similar to tissue in FIGS. 8A and 8B. For simplicity, we assume a two-dimensional geometry and a region of interest of length 32×l* along x and of length 32×l* along z, where the transport mean free path length l*=3D. FIGS. 8A and 8B show localization of a single source of fluorescence (K=1) using an (x,z) coordinate system. One source (green) and seven detectors (red) are placed at the boundary of a square of side length 32l*, where l*=0.5 mm, and we assume an SNR of 30 dB. A source of fluorescence with $\rho_1$=0.1 mm$^{-1}$ was placed at x=15.26×l* and z=15.56×l*. The simulated noisy data is the same as the first set of curves at $\tau_1$ shown in FIG. 7B. FIG. 8A shows $\tilde{\rho}_k(r_{f_k})$ obtained from (21) plotted over the region of interest. FIG. 8B shows the cost $c_k(r_{f_k}, \tau_k)$ from (21) plotted over the region of interest. The position with lowest cost in (b) is $\tilde{r}_{f_k}$, and the value of $\tilde{\rho}_k$ and $\tilde{r}_{f_k}$ in (a) is $\tilde{\rho}_k$. Here, $\tilde{r}_{f_k}$=(x, z)=(15.24, 15.75)×l* and $\tilde{\rho}_k$=0.0999 mm$^{-1}$, which are close to the true values. The percent errors in the estimated x and z positions are 0.143% and 1.196%, respectively. The discretization of the region of interest is a primary contributor to the estimation error. We calculated the localization error as $[(r_{f_k} - \tilde{r}_{f_k})/r_{f_k} \times 100]\%$. The results can be extrapolated to three dimensions, and the problem is scalable in the amount of scatter.

Figure 9:
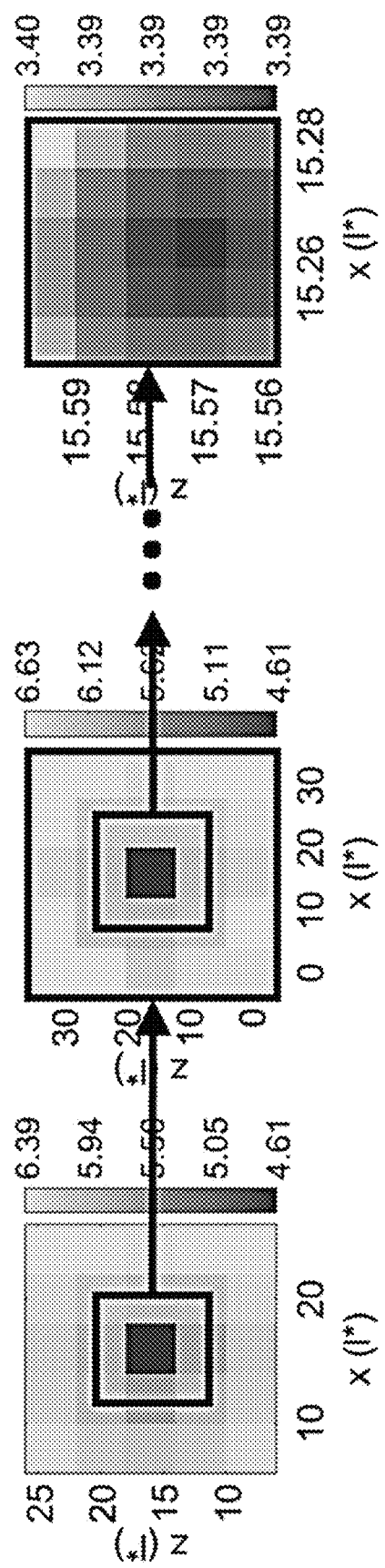
FIG. 9 is a graphical representation of a multiresolution analysis (MRA) methodology according to the present disclosure.

We introduce a method to simultaneously reduce the computation time and improve the accuracy of the localization by incorporating a hierarchy of discretization grids into the localization. We refer to this as a multiresolution analysis (MRA) method, and it is demonstrated in FIG. 9. First, $c_k(r_{f_k}, \tau_k)$ is calculated using (21) on a coarse grid over the entire region of interest. Then, $c_k(r_{f_k}, \tau_k)$ is iteratively calculated on successively smaller and finer grids, such that each new grid contains the point of minimum cost of the current iteration. This procedure is repeated until convergence, which, in our case, was based on two successive grids where the change in the minimum cost was less than 1%, but not equal to zero. Importantly, not converging when the change in cost is zero avoids the situation where the same point happens to have the lowest cost on two grids. Each new grid contains the region of smallest cost. Here, $\tilde{r}_{f_k}$=(x, z)=(15.27, 15.57)×l* and $\tilde{\rho}_k$0.1003 mm$^{-1}$. The percent errors in the estimated x and z positions are 0.037% and 0.066%, respectively. The discretization error has been reduced, especially for the z coordinate. The number of positions where the cost must be calculated has also been reduced, decreasing the computation time. The reduction is even greater when extrapolated to 3D.

We show localization of four different sources of fluorescence separated by varying delays. We use the same geometry and optical parameters as in FIGS. 8A and 8B, except we place four sources of fluorescence within the medium instead of one.

Figure 10C:
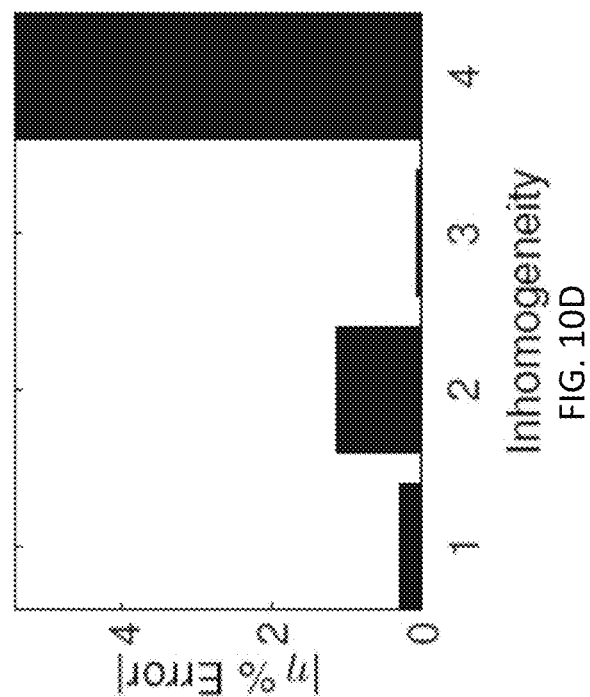
FIG. 10C is a plot of the actual and predicted locations of the inhomogeneities, which are separated by a specific length.
Figure 10D:
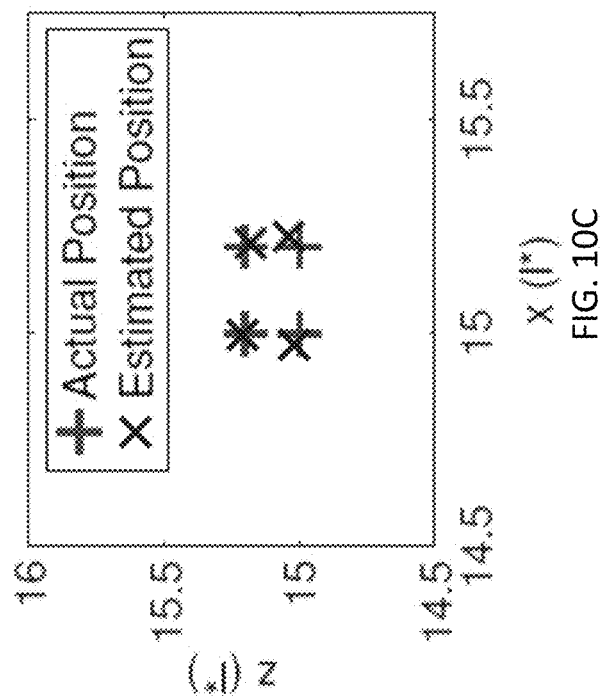
FIG. 10D is plot of the calculated yield for four inhomogeneity.

FIG. 10A shows the problem geometry as in FIGS. 8A and 8B, where the positions of the excitation source (green), detectors (red), and fluorophores (cyan) are shown. FIG. 10B shows the simulated noisy data from the four inhomogeneities with delays of 0.9, 3.75, 7.5, and 8.6 ns. The first two inhomogeneities are temporally separated, while the second two have a significant temporal overlap. FIG. 10C plots the actual and predicted locations of the inhomogeneities, which are separated by 0.2×l*. FIG. 10D shows the yield ρ (proportional to concentration) experimental errors, calculated as $[(\rho_k-\tilde{\rho}k)/(\rho_k \times 100)]$. For the multiresolution operation, we used $N_x=N_z=5$ equally spaced points for each grid, the same as what was used in FIG. 9. The first coarse grid was defined over the entire square region of interest from FIGS. 8A and 8B, and each finer square grid was centered at (21) and extended a distance slightly greater than the previous grid spacing along the x and z directions (similar to FIG. 9). Both the position and II were predicted with high accuracy, even for the case when there is overlap between the temporal signals.

For high spatial resolution localization, we assume insignificant background signal and that the fluorophores do not diffuse or change positions significantly during the integration time. In this case, the localization uncertainty is dominated by measurement noise and each $\tilde{r}_{kf}$ coordinate x and z has a Gaussian probability distribution characterized by the standard deviations $\sigma_x$ and $\sigma_z$. These standard deviations are commonly used to characterize the spatial precision of localization. Here, we show the capability of localization to extract high-spatial-resolution information by generating these statistics from numerical calculations.

We iteratively localize the single emitter in FIGS. 8A and 8B using MRA, and the results are shown in FIGS. 11A-11F. During each iteration, random noise was added to the forward calculation in order to generate independent simulated measurements. Both $\sigma_x$ and $\sigma_z$ were then calculated from the localized positions and used to plot ellipses with major and minor axis equal to $4\sigma_x$ or $4\sigma_z$.

Figure 11B:
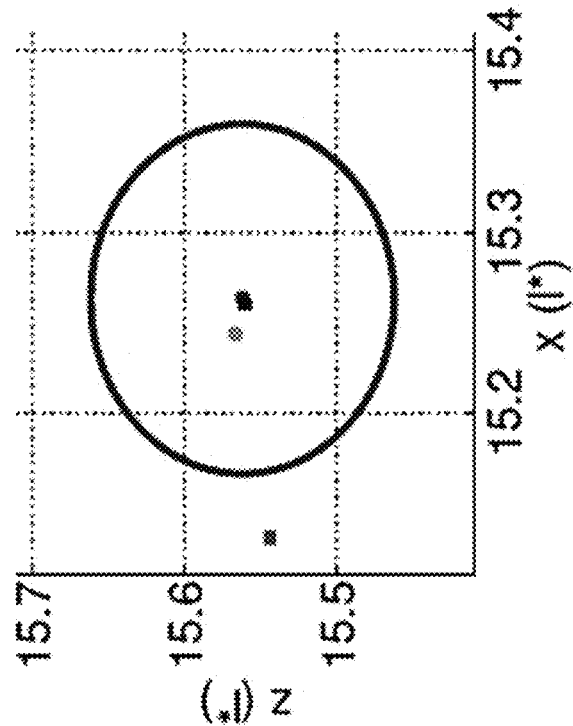
FIGS. 11A and 11B are graphs of localization uncertainly statistics for different SNR, where the noise was added.
Figure 11A:
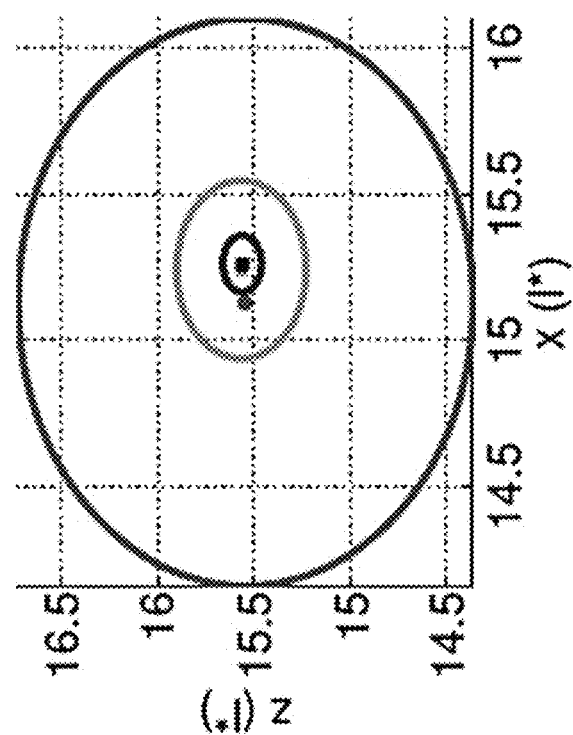
Figure 11D:
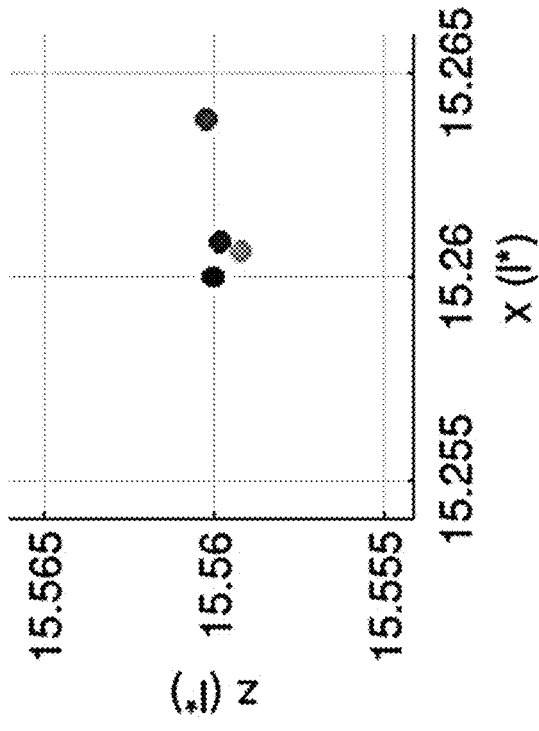
FIGS. 11C and 11D are localization uncertainly statistics for different numbers of detectors.
Figure 11C:
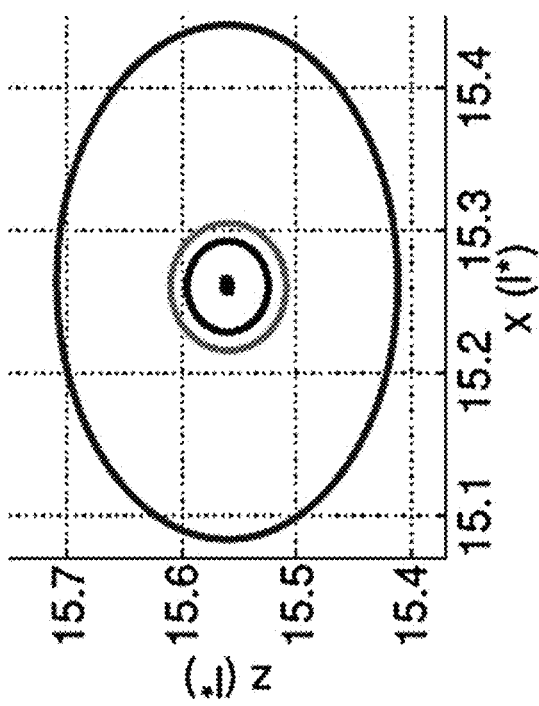

FIGS. 11A and 11B show localization uncertainly statistics for different SNR, where the noise was added. Even for a low SNR of 10 dB, the location of the fluorescent inhomogeneity can be estimated with much higher accuracy compared to traditional diffusive imaging methods. FIGS. 11C and 11D show localization uncertainly statistics for different numbers of detectors M. The detectors were distributed as in FIGS. 8A and 8B, and the statistics depend on the spatial support. Compared to volumetric image reconstruction with FDOT, little information, or fewer detectors, are needed to localize the fluorophore.

Figure 11F:
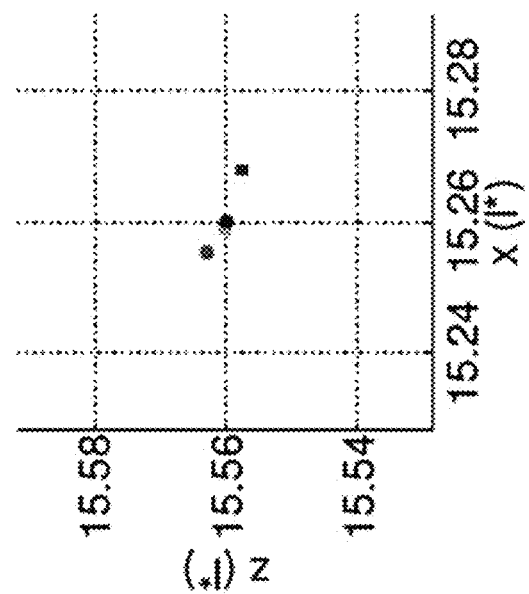
FIGS. 11E and 11F are localization uncertainly statistics for different parameters.
Figure 11E:
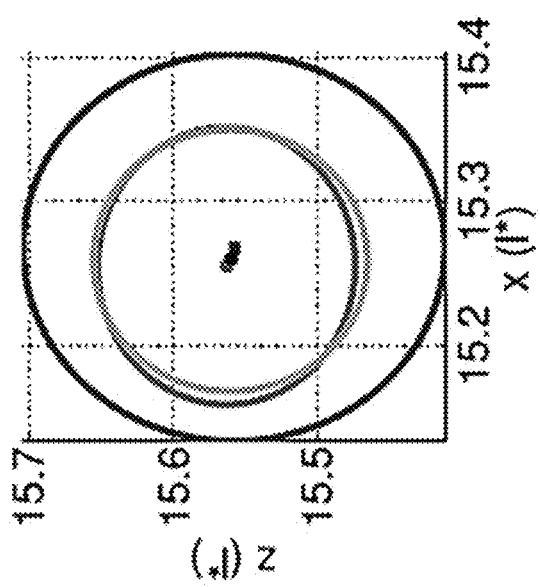

It is not clear how or if the localization uncertainty will depend on the window length w. To study this, we build up localization uncertainly statistics for different w with a constant SNR of 30 dB and M=7. The results are shown in FIGS. 11E and 11F. For all results in FIGS. 11A-11F, the time axis starts at t=0 and continues in increments of T=0.19 ns for 64 increments, giving $t_{max}$=12.16 ns. As can be seen in FIGS. 11E and 11F, the localization statistics change slightly with window size, but they are still highly accurate even for the shortest window of length 2T.

The localization uncertainty of the sources of fluorescence in FIG. 10C is described by the blue ellipse in FIG. 11B. The extension to imaging is straightforward. If we consider an image which is made up of voxels, and each voxel can be individually localized, then FIGS. 11A-11F describes the resolution limit of the image. The resolution limit of FIG. 11B, or the minimum distance between two sources of fluorescence, such that they can both be accurately localized, is about 0.1l* or 50 μm. This is a remarkable spatial resolution for deep tissue optical imaging.

Figure 12:
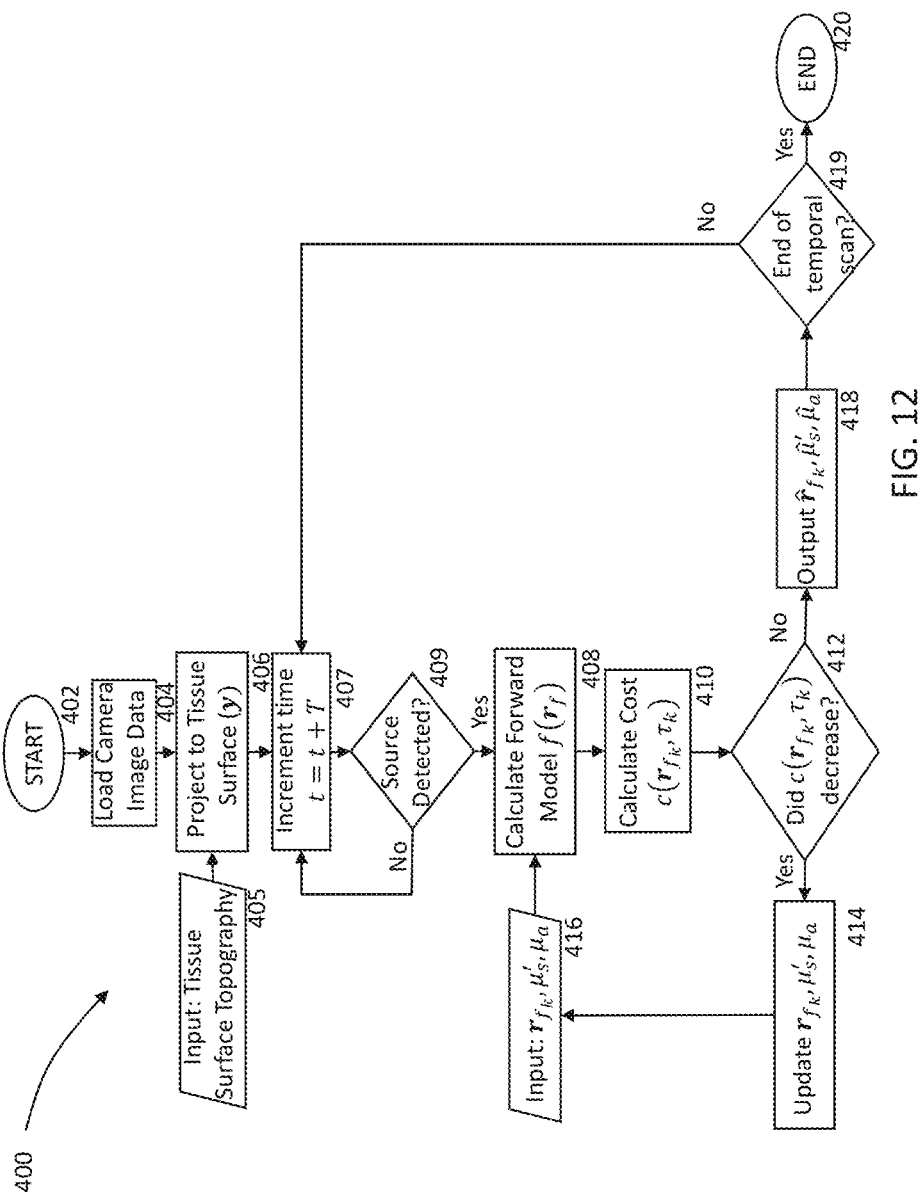
FIG. 12 is a flowchart describing steps of modeling, according to one embodiment of the present disclosure.

Referring to Referring to FIG. 12, a flowchart of a process 400 is shown which is the basis of the temporal modeling, according to the present disclosure. The process 400 starts out at the start block 402 and proceeds to loading camera image data, block 404. This data represents the filtered (i.e., fluoresced light emitted from a source of fluorescence in an otherwise homogeneous tissue allowed to pass through the filter 122 (see FIG. 1)). This step represents capture of at least one 2-dimensional (2D) image of a subject having a plurality of pixels. A region of interest is thus identified. Next a 3D topography data of the subject is established as shown in block 405. This topography data is established by one of many approaches known to a person having ordinary skill in the art. For example, laser scanning of the subject can be used to establish the 3D topography data. Another example is a stereoscopic approach using stereo cameras. The 3D topography data is fed to the processor which maps the 2D image at least about the region of interest to the 3D topography data. This is done in block 406. A time is then started in block 407 and incremented. In decision block 409, the processor determines if a source of fluorescence is detected. If not, then the process 400 returns to the timer block 407. If yes, then the process 400 processed to block 408. Next in block 408 a forward model solution is generated. The model is a mathematical model representing physical properties of light propagation through the source of fluorescence and homogeneous tissue based on the 3D topography data including a plurality of parameters defining the model. The model is adapted to provide a model representation of the at least one 2D captured image based on spatial and temporal parameters discussed above. Next in block 410 a cost function is calculated based on comparison of the modeled at least one 2D captured image to the actual captured of the at least 2D image. The cost function represents an error signal representing a difference therebetween. In the decision block 412 the cost function is compared to the last iteration; if the cost decreased (i.e., still not at the minimum), then the parameters of the model $(r_{f_k}, \mu'_s, \mu_a)$ are updated in block 414 and provided to the model as updates in block 416. Otherwise (i.e., the cost function is at the minimum), the parameters are provided to the model at block 418. At this point, the processor determine whether the temporal scan has ended in decision block 419 based on whether the system has measured data for a predetermined amount of time. If not, the process 400 proceeds back to the timer block 407 and repeats the previous steps. If yes, then the optimization of the model ends in block 420. The model can then output the location and geometric dimensions, location, and timing of the neurons to be used for further processing (e.g., studying neurons and how they fire).

Those having ordinary skill in the art will recognize that numerous modifications can be made to the specific implementations described above. The implementations should not be limited to the particular limitations described. Other implementations may be possible.

The invention claimed is:

1. A system for spatially and temporally mapping neurons in brain tissue, comprising:
   a light source configured to be shone on a subject, the light source configured to illuminate brain tissue of the subject at a first wavelength, and in response cause emission of light at a second wavelength from generating calcium when one or more neurons are firing;

an optical filter configured to filter out light having the first wavelength and allow passage of light having the second wavelength;

an image capture device comprising a charge-coupled device configured to capture at least one 2-dimensional (2D) image having a plurality of pixels of the brain tissue at the second wavelength; and a processor configured to establish information about approximate location of the one or more neurons in the 2D captured image, identify a region of interest about the approximate location of the one or more neurons, establish a 3D topography data of the subject at least about the region of interest, map each pixel of the region of interest of the at least one 2D captured image to the 3D topography data, selectively generate the 3D geometric spatial-temporal model based on a plurality of parameters including optical parameters of the brain tissue as well as the mapped pixels of the region of interest on the 3D topography data, wherein the spatial-temporal model outputs a spatial-temporal modeled 2D image representation of the at least one 2D captured image, compare the spatial-temporal modeled 2D image to the at least one 2D captured image and generate an error signal representing a difference therebetween, iteratively adjust the plurality of parameters of the 3D spatial-temporal model to minimize the error signal, and output the 3D spatial-temporal model of the firing of the one or more neurons within the brain tissue within the region of interest.

2. The system of claim 1, wherein establishment of the 3D topography data is based on laser scanning.

3. The system of claim 1, wherein establishment of the 3D topography data is based on stereoscopic image acquisition.

4. The system of claim 3, the stereoscopic image acquisition using at least two image capture devices.

5. The system of claim 1, wherein the establishment of information about approximate location of the one or more neurons is by causing the one or more neurons to fluoresce.

6. The system of claim 1, the establishment of information about the approximate location of one or more neurons is by analyzing scattered light initially shone from the light source.

7. The system of claim 1, the establishment of information about approximate location of the one or more neurons is by analyzing absorption of light initially shone from the light source.

8. The system of claim 1, wherein the light source is a laser light.

9. The system of claim 8, wherein the laser light is spread using a light spreader.

\* \* \* \* \*